US006210894B1

(12) United States Patent
Brennan (10) Patent No.: US 6,210,894 B1
(45) Date of Patent: **\*Apr. 3, 2001**

(54) METHOD AND APPARATUS FOR CONDUCTING AN ARRAY OF CHEMICAL REACTIONS ON A SUPPORT SURFACE

(75) Inventor: Thomas M. Brennan, San Francisco, CA (US)

(73) Assignee: Protogene Laboratories, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/314,456

(22) Filed: May 18, 1999

Related U.S. Application Data

(63) Continuation of application No. 08/465,761, filed on Jun. 6, 1995, now Pat. No. 5,985,551, which is a continuation of application No. 08/068,540, filed on May 27, 1993, now Pat. No. 5,474,796, which is a continuation-in-part of application No. 07/754,614, filed on Sep. 4, 1991, now abandoned.

(51) Int. Cl.$^7$ .................................................. C12Q 1/68
(52) U.S. Cl. ............................................. 435/6; 536/23.1
(58) Field of Search ................................ 435/6; 536/23.1

(56) References Cited

U.S. PATENT DOCUMENTS

| | | |
|---|---|---|
| 3,736,042 | 5/1973 | Markozits et al. . |
| 5,063,081 | 11/1991 | Cozzette et al. . |
| 5,143,854 | 9/1992 | Pirrung et al. . |
| 5,252,743 | 10/1993 | Barrett et al. . |
| 5,412,087 | 5/1995 | McGall et al. . |
| 5,424,186 | 6/1995 | Fodor et al. . |
| 5,445,934 | 8/1995 | Fodor et al. . |
| 5,449,754 | 9/1995 | Nishioka . |
| 5,474,796 | 12/1995 | Brennan . |
| 5,510,270 | 4/1996 | Fodor et al. . |

FOREIGN PATENT DOCUMENTS

| | | |
|---|---|---|
| 0 161 058 A1 | 11/1985 | (EP) . |
| 373203 | 8/1994 | (EP) . |
| WO 90/03382 | 4/1990 | (WO) . |
| WO 90/15070 | 12/1990 | (WO) . |

OTHER PUBLICATIONS

Fodor, et al., Light–Directed, Spatially Addressable Parallel chemical Synthesis, *Science 251*:767–773 (1991).
Ramirez, Levy, Ringold, Rosenkranz, Wiley, Esterie, Bailey, and Mintha *J. Organic Chemistry 21*:1333–1335 (1956).

Khrapko, et al. An Oligonucleotide by Hybridization Approach to DNA Sequencing, *FEBS Letters 256*: 118–122 (1989).

Drmanac, et al., Sequencing of Megabase Plus DNA by Hybridization Theory of the Method, *Genomic 4*: 114–128 (1989).

Geysen, et al., Strategies for Epitope Analysis Using Peptide Synthesis, *J. Immunol. Methods 102*:259–274 (1987).

Southern and Maskos, Support–bound Oligonucleotides, *Chem Abst.*, —Abstract No. 152979r, *113*: 152984 (1990).

Mandenius, et al., Reversible and Specific Interaction of Dehydrogenases with a Coenzyme–Coated Surface Continuously Monitored with a Reflectometer, *Anal. Biochem. 157*:283–288 (1986).

Southern and Maskos, Analysing Nucleic Acids by Hybridisationof Oligonucleotides: Analysis of Mutations, Abstracts of papers presented at the 1991 meeting fo Genome Happing and Sequencing, Cold Spring Harbor Laboratory, Cold Spring Harbor, N.Y. (1991).

Froehler, et al., Synthesis of DNA via Deoxynucleoside H–phosphonate Intermediates, *Nuc. Acids Res. 14*:5399–5407 (1986).

Kyser, et al., Design of an Impulse Ink Jet, *J. Applied Photographic Engineering 7*:73–79 (1981).

Drmanac, et al., Reliable Hybridization of Oligonucleotides as Short as Six Nucleotides, *DNA an Cell Biology 9*:527–534 (1990).

McGraw, et al., Sequence–Dependent Oligonucleotide–Target Duplex Stabilities: Rules from Empirical Studes with a Set of Twenty–Mers, *Biotechniques 8*:674–678 (1990).

Wood, et al., Base Composition–Independent Hybridization in Tetramethylammonium Chloride: A Method for Oligonucleotide Screening of Highly Complex Gene Libraries, *PNAS USA 82*:1585–1588 (1985).

*Primary Examiner*—Scott W. Houtteman
(74) *Attorney, Agent, or Firm*—Albert P. Halluin; Wallace Wu; Howrey Simon Arnold & White, LLP (57) ABSTRACT

The invention provides apparatus and methods for making arrays of functionalized binding sites on a support surface. The invention further provides apparatus and methods for sequencing oligonucleotides and for identifying the amino acid sequence of peptides that bind to biologically active macromolecules, by specifically binding biologically active macromolecules to arrays of peptides or peptide mimetics.

19 Claims, 8 Drawing Sheets

```
            A    C
                         Matrix                    (a)
            G    T
```

```
AAA  AAC  ACA  ACC  CAA  CAC  CCA  CCC
AAG  AAT  ACG  ACT  CAG  CAT  CCG  CCT
AGA  AGC  ATA  ATC  CGA  CGC  CTA  CTC
AGG  AGT  ATG  ATT  CGG  CGT  CTG  CTT
GAA  GAC  GCA  GCC  TAA  TAC  TCA  TCC      (b)
GAG  GAT  GCG  GCT  TAG  TAT  TCG  TCT
GGA  GGC  GTA  GTC  TGA  TGC  TTA  TTC
GGG  GGT  GTG  GTT  TGG  TGT  TTG  TTT
```

(with ATT, GCC, CTT, TCT, TTA, TTC, GTT, TGT, TTG underlined/bold)

```
        DNA Fragment
     -----ATTCTTGTTA---

ATT
         TTC                    TTA, TTG
          TCT
           CTT
            TTG                  TTA              (c)
             TGT
              GTT
               TTA
```

Correct Assembly        Possible N+1 List

METHOD AND APPARATUS FOR CONDUCTING AN ARRAY OF CHEMICAL REACTIONS ON A SUPPORT SURFACE

This is a continuation of Ser. No. 08/465,761, filed Jun. 6, 1995, now U.S. Pat. No. 5,985,551; which is a continuation of Ser. No. 08/068,540, filed May 27, 1993, now U.S. Pat. No. 5,474,796; which is a continuation-in-part of Ser. No. 07/754,614, filed Sep. 4, 1991, abandoned.

BACKGROUND OF THE INVENTION

1. Field of the Invention

The invention relates to methods for conducting a large number of chemical reactions on a support surface, methods for making the support surface, and the support surface itself.

2. Summary of the Related Art

Proposals for the direct sequencing of DNA by hybridization with arrays of oligonucleotides are known in the art. Drmanac et al., Genomics 4; 114 (1989) proposes hybridization array-mediated DNA sequencing by binding target DNA to a dot blot membrane, followed by probing with an array of oligonucleotides. Khrapko et al., FEBS Letters 256, 118 (1989) proposes hybridization array-mediated DNA sequencing by binding the oligonucleotide array to a support membrane, followed by probing with target DNA.

Synthesis of arrays of bound oligonucleotides or peptides is also known in the art. Houghton, in the Multiple Peptide System product brochure describes the T-bag method, in which an array of beads is physically sorted after each interaction. This method becomes unwieldy for the preparation of large arrays of oligonucleotides. Geysen et al., J. Immunol. Methods 102; 259 (1987) discloses the pin method for the preparation of peptide arrays. The density of arrays that may be produced by this method is limited, and the dipping procedure employed in the method is cumbersome in practice. Southern, Genome Mapping and Sequencing Conference, May 1991, Cold Spring Harbor, N.Y., disclosed a scheme for oligonucleotide array synthesis in which selected areas on a glass plate are physically masked and the desired chemical reaction is carried out on the unmasked portion of the plate. In this method it is necessary to remove old mask and apply a new one after each interaction. Fodor et al., Science 251; 767 (1991) describes a method for synthesizing very dense 50 micron arrays of peptides (and potentially oligonucleotides) using mask-directed photochemical deprotection of synthetic intermediates. This method is limited by the slow rate of photochemical deprotection and by the susceptibility to side reactions (e.g., thymidine dimer formation) in oligonucleotide synthesis. Khrapko et al, FEBS Letters 256; 118 (1989) suggests simplified synthesis and immobilization of multiple oligonucleotides by direct synthesis on a two dimensional support, using a printer-like device capable of sampling each of the four nucleotides into given dots on the matrix. However, no particulars about how to make or use such a device are provided.

Some methods for permanently attaching oligonucleotides to glass plates in a manner suitable for oligonucleotide synthesis are known in the art. Souther, Chem. abst. 113; 152979r (1990) describes a stable phosphate ester linkage for permanent attachment of oligonucleotides to a glass surface. Mandenius et al., Anal. Biochem. 157; 283 (1986) teaches that the hydroxyalkyl group resembles the 5'-hydroxyl of oligonucleotides and provides a stable anchor on which to initiate solid phase synthesis.

The related art contains numerous ideas and information related to arrays of chemical reactants on a solid support. However, existing or suggested methods are limited, and do not conveniently and reliably produce the very large, high density arrays. There is, therefore, a need for new methods for preparing large high density arrays of reactive sites. Ideally, such methods should utilized relatively simple machinery to produce large, dense arrays of solid phase bound reactants in a reproducible and rapid manner.

SUMMARY OF THE INVENTION

This invention provides a method for conducting a large number of chemical reactions on a support surface. Solutions of chemical reactants are added to functionalized binding sites on the support surface by means of a piezo-electric pump. This pump deposits microdroplets of chemical reactant solution onto the binding sites. The chemical reactant at each binding site is separated from the others by surface tension. Typically, the support surface has $10–10^4$ functionalized binding sites per $cm^2$ and each functionalized binding site is about 50–2000 microns in diameter. Typically, the amounts of reagents added to each binding site is in a volume of about 50 picoliter to 2 microliter. The reactions at the functionalized binding site may form covalent bonds such as esters or amide bonds or may involve non-covalent specific binding reactions such as antibody/antigen binding or oligonucleotide specific binding. The invention also includes array plates and methods for making the array plates.

Figure 2A:
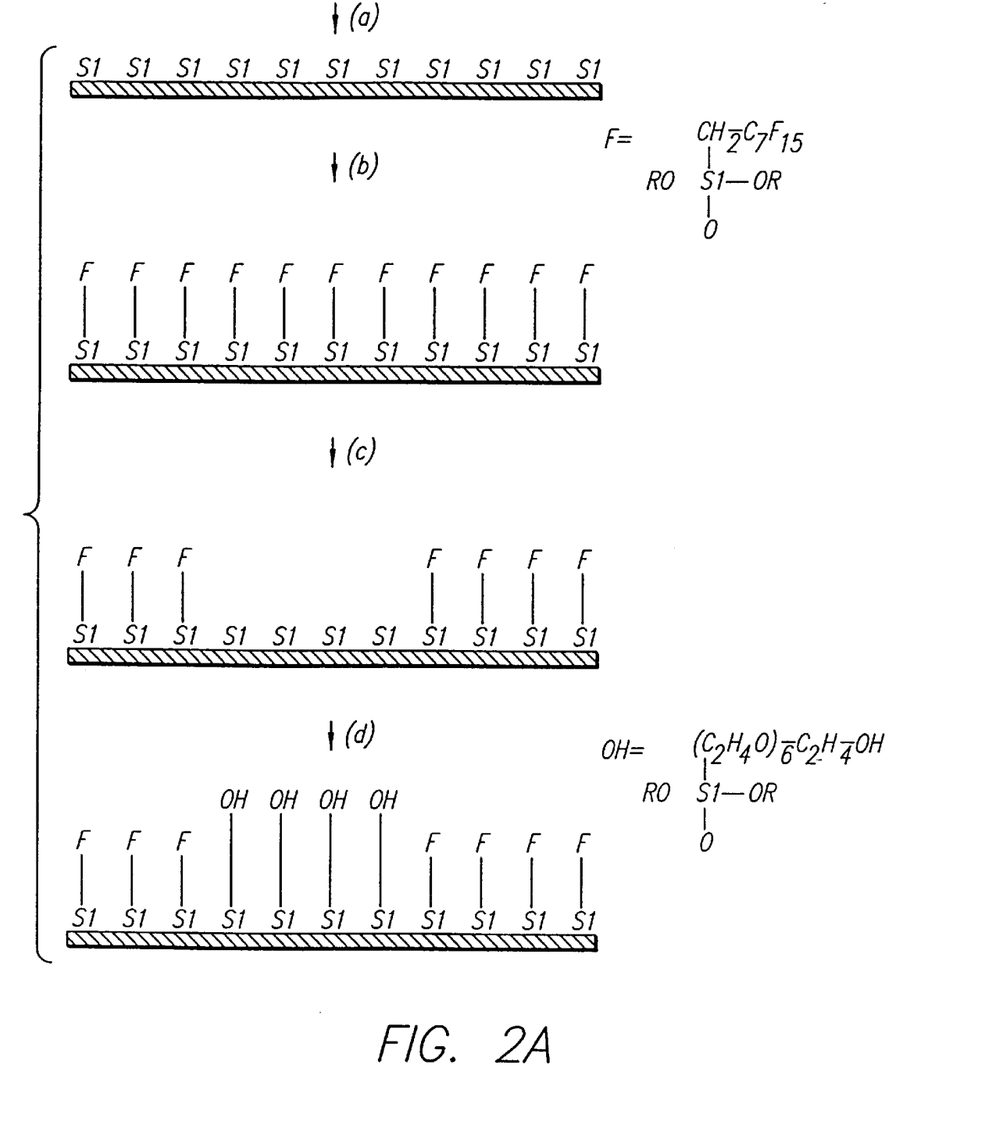
FIG. 2A: Illustrates the formation of an array surface that is ready for solid phase synthesis.

Typically, the array plates are made by the process set out in FIG. 2A by (a) coating a support surface with a positive or negative photoresist substance which is subsequently exposed and developed to create a patterned region of a first exposed support surface;

(b) reacting the first support surface with a fluoroalkylsilane to form a stable fluoroalkylsiloxane hydrophobic matrix on the first support surface;

(c) removing the remaining photoresist to expose a second support surface; and (d) reacting the second support with a hydroxy or aminoalkylsilane to form derivatized hydrophilic binding site regions. The preferred siloxane reaction product of the present invention is tridecafluoro 1,1,2,2-tetrahydrooctyl siloxane. In FIG. 2A, the hatched lines are the solid support, "SI" represents a first exposed support surface site, "SI-F" is a hydrophobic fluoroalkylsilane site, and "SI-OH" is a derivatized hydrophilic binding site.

Figure 2B:
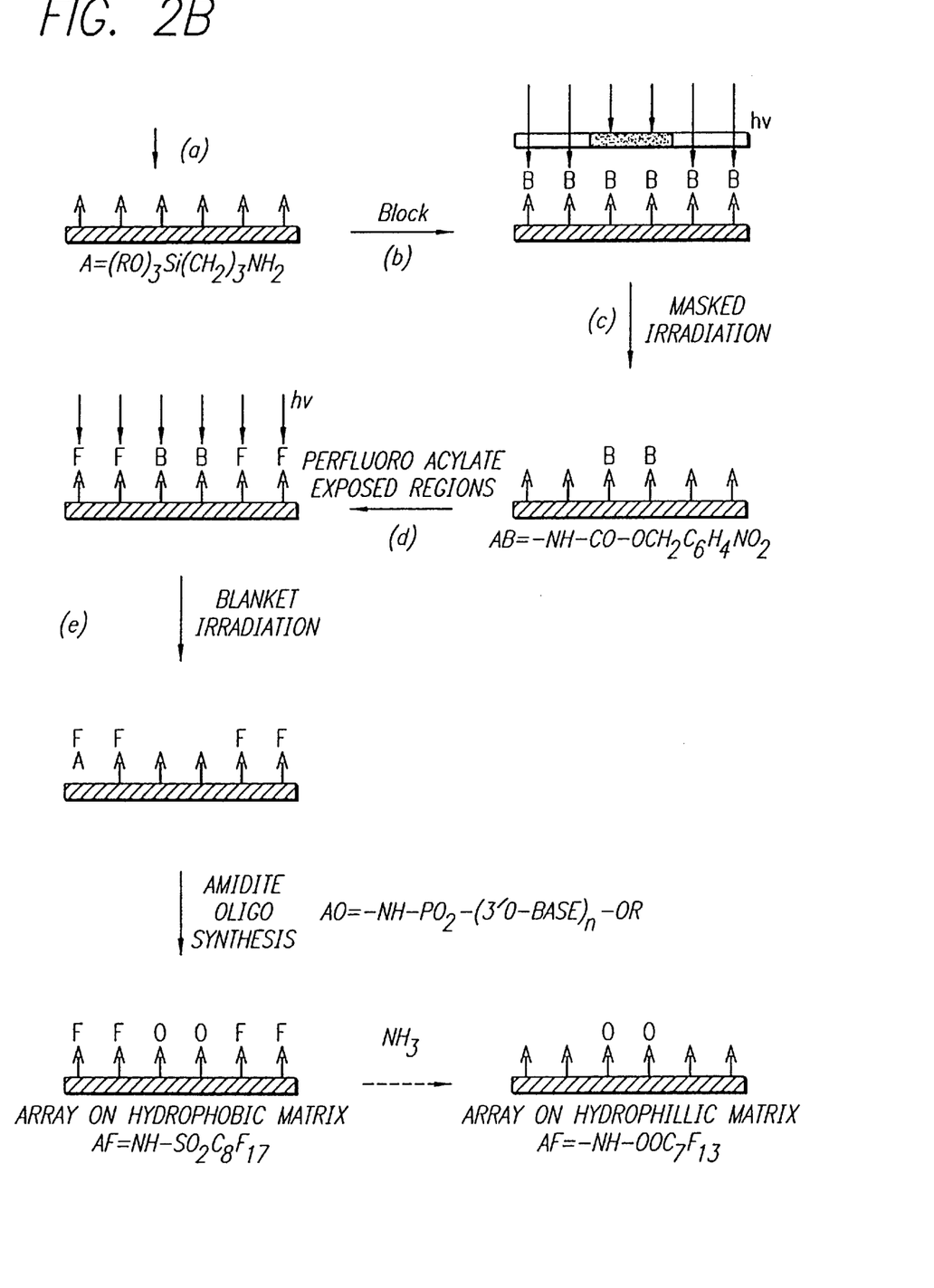
FIG. 2B: Illustrates O-Nitrocarbamate array making chemistry.

Alternatively, the array plates can be made by the process set out in FIG. 2B by (a) reacting a support surface with a hydroxy or aminoalkylsilane to form a derivatized hydrophilic support surface;

(b) reacting the support surface form step (a) with o-nitrobenzyl carbonyl chloride as a temporary photolabile blocking to provide a photoblocked support surface;

(c) exposing the photoblocked support surface of step (b) to light through a mask to create unblocked areas on the support surface with unblocked hydroxy or aminoalkylsilane;

(d) reacting the exposed surface of step (c) with perfluoroalkanoyl halide or perfluoroalkylsulfonyl halide to form a stable hydrophobic (perfluoroacyl or perfluoroalkylsulfonamido) alkyl siloxane matrix; and (e) exposing this remaining photoblocked support surface to create patterned regions of the unblocked hydroxy- or aminoalkylsilane to form the derivatized hydrophilic binding site regions. The preferred siloxanes of the present invention are 3-perfluorooctanoyloxy propylsiloxane and 3-perfluorooctanesulfonamido propylsiloxane. In FIG. 2B, the hatched lines are the solid support, "-A" represents a hydrophilic support site, "-A B" represents a temporary photolabile blocked support site, and "-A F" represents a hydrophobic site.

The invention also provides a method for determining or confirming the nucleotide sequence of a target nucleic acid. The target nucleic acid is labelled by conventional methods and hybridized to an oligonucleotides of known sequence previously bound to sites on the array plate. The array plate having bound labelled target nucleic acid is then washed at appropriate stringency and the presence and location of bound labelled target nucleic acid is determined using scanning analyzers. Since the sequence of the covalently attached oligonucleotide in each element on the array is known, this allows the unambiguous determination of the nucleotide sequence of the target nucleic acid.

The methods of the invention may also be applied to the determination of peptides or peptide mimetics that bind biologically active receptors. In this aspect, peptide arrays of known sequence can be applied to glass plates using the same piezoelectric pump/surface tension wall method described supra. The resulting array of peptides can then be used in binding analyses with biologically active receptor ligands to screen for peptide mimetics of receptor agonists and antagonists. Thus, the invention provides a method for producing peptide array plates, peptide array plates having covalently bound peptides separated by surface tension areas, and methods of using such peptide array plates to screen for peptide mimetics of receptor agonists and antagonists.

Those skilled in this art will recognize a wide variety of binding site and chemical reactants for forming either covalent bonds or for specific binding reagents.

DETAILED DESCRIPTION OF THE INVENTION

The practice of present invention can include a number of photoresist substances. These substances are readily known to those of skill in the art. For example, an optical positive photoresist substance (e.g., AZ 1350 (Novolac™ type-Hoechst Celanese™) (Novolac™ is a proprietary novolak resin, which is the reaction product of phenols with formaldehyde in an acid condensation medium)) or an E-beam positive photoresist substance (e.g., EB-9 (polymethacrylate by Hoya™)) can be used.

A number of siloxane functionalizing reagents can be used, for example:
1. Hydroxyalkyl siloxanes (Silylate surface, functionalize with diborane, and $H_2O_2$ to oxidize the alcohol)
   a. allyl trichlorochlorosilane →→3-hydroxypropyl
   b. 7-oct-1-enyl trichlorochlorosilane →→8-hydroxyoctyl
2. Diol (dihydroxyalkyl) siloxanes (silylate surface, and hydrolyze to diol)
   a. glycidyl trimethoxysilane →→(2,3-dihydroxypropyloxy)propyl
3. Aminoalkyl siloxanes (amines require no intermediate functionalizing step)
   a. 3-aminopropyl trimethoxysilane →3-aminopropyl
4. Dimeric secondary aminoalkyl siloxanes
   a. bis(3-trimethoxysilylpropyl) amine →bis (silyloxylpropyl) amine In addition, a number of alternative functionalized surfaces can be used in the present invention. These include the following:
1. Polyethylene/polypropylene functionalized by gamma irradiation or chromic acid oxidation, and reduction to hydroxyalkyl surface.
2. Highly crosslinked polystyrene-divinylbenzene derivatized by chloromethylation, and aminated to benzylamine functional surface.
3. Nylon—the terminal aminohexyl groups are directly reactive.
4. Etched, reduced polytetrafluoroethylene.

There are two important characteristics of the masked surfaces in patterned oligonucleotide synthesis. First, the masked surface must be inert to the conditions of ordinary oligonucleotide synthesis; the solid surface must present no free hydroxy, amino or carboxyl groups to the bulk solvent interface. Second, the surface must be poorly wet by common organic solvents such as acetonitrile and the glycol ethers, relative to the more polar fuctionalized binding sites.

The wetting phenomenon is a measure of the surface tension or attractive forces between molecules at a solid-liquid interface, and is defined in dynes/$cm^2$. Fluorocarbons have very low surface tension because of the unique polarity (electronegativity) of the carbon-flourine bond. In tightly structured Langmuir-Blodgett type films, surface tension of a layer is primarily determined by the percent of fluorine in the terminus of the alkyl chains. For tightly ordered films, a single terminal trifluoromethyl group will render a surface nearly as lipophobic as a perfluoroalkyl layer. When fluorocarbons are covalently attached to an underlying derivatized solid (highly crosslinked polymeric) support, the density of reactive sites will generally be lower than Langmuir-Blodgett and group density. However, the use of perfluoroalkyl masking agents preserves a relatively high fluorine content in the solvent accessible region of the supporting surface.

There are also two important characteristics of the derivatized regions in patterned oligonuclcotide synthesis. The surface must be compatible with the method of detection of hybridization. Radioactivity is largely being replaced by spectroscopic, chemiluminescent and fluorescent detection techniques in DNA research. It is desirable that the surface be optically transparent. A second important characteristic is that the linkage of the penultimate oligonucleotide to the surface have high chemical stability, at least equal to that of the polyphosphate backbone in DNA.

The optical properties of glass (polytetrasiloxane) are unsurpassed for detection purposes. Further, there are numerous techniques developed by the semiconductor industry using thick films (1–5 microns) of photoresists to generate masked patterns of exposed glass surfaces. The best method to derivatize the first exposed glass surface is with volatile fluoroalkyl silanes using gas phase diffusion to create closely packed lipophobic monolayers. The polymerized photoresist provides an effectively impermeable barrier to the gaseous fluoroalkyl silane during the time period of derivatization of the exposed region. Following lipophobic derivatization however, the remaining photoresist can be readily removed by dissolution in warm organic solvents (methyl, isobutyl, ketone, or N-methyl pyrrolidone) to expose a second surface of raw glass, while leaving the first applied silane layer intact. This second region glass can then be derivatized by either solution or gas phase methods with a second, polar silane which contains either a hydroxyl or amino group suitable for anchoring solid phase oligonucleotide synthesis.

Siloxanes have some what limited stability under strongly alkaline conditions. Conditions such as 0.1 N sodium hydroxide, typically employed to strip probes from nylon hybridization membranes, should be avoided for reusable glass based hybridization arrays.

Teflon (polytetrafluoroethylene) itself would provide an ideal lipophobic surface. Patterned derivatization of this type of material can be accomplished by reactive ion or plasma etching through a physical mask or using an electron beam, followed by reduction to surface hydroxymethyl groups. However, the opacity of teflon at visible wavelengths severely restrict the applicable methods for detection of hybridization.

Depending on the ultimate application, other organic polymers have desirable characteristics for patterned oligonucleotide synthesis. Polypropylene is relatively transparent to visible light. It can be surface derivatized by chromic acid oxidation, and converted to hydroxy- or aminomethylated surfaces which provide oligonucleotide synthesis anchors of high chemical stability. Highly crosslinked polystryene-divinylbenzene (ca. 50%) is non-swellable, and can be readily surface derivatized by chloromethlylation and subsequent functional group manipulation. Nylon provides an initial surface of hexylamino groups.

The lipophobic patterning of these surfaces can be effected using the same type of solution based thin film masking techniques and gas phase derivatization as glass, or by direct photochemical patterning using o-nitrobenzylcarbonyl blocking groups. Perfluoroalkyl carboxylic and sulfonic acid derivatives rather than silanes are now used to provide the lipophobic mask of the underlying surface during oligonucleotide synthesis.

Figure 5A:
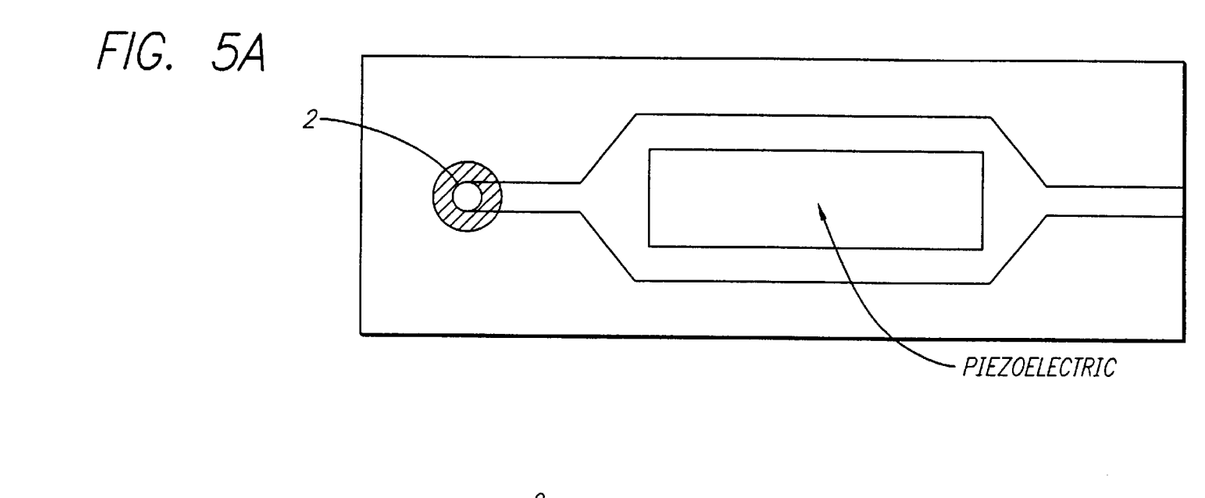
FIGS. 5A,B: Top and side views of a piezoelectric impulse jet of the type used to deliver solid phase synthesis reagents to individual dots in the array plate synthesis methods according to the invention.
Figure 5B:
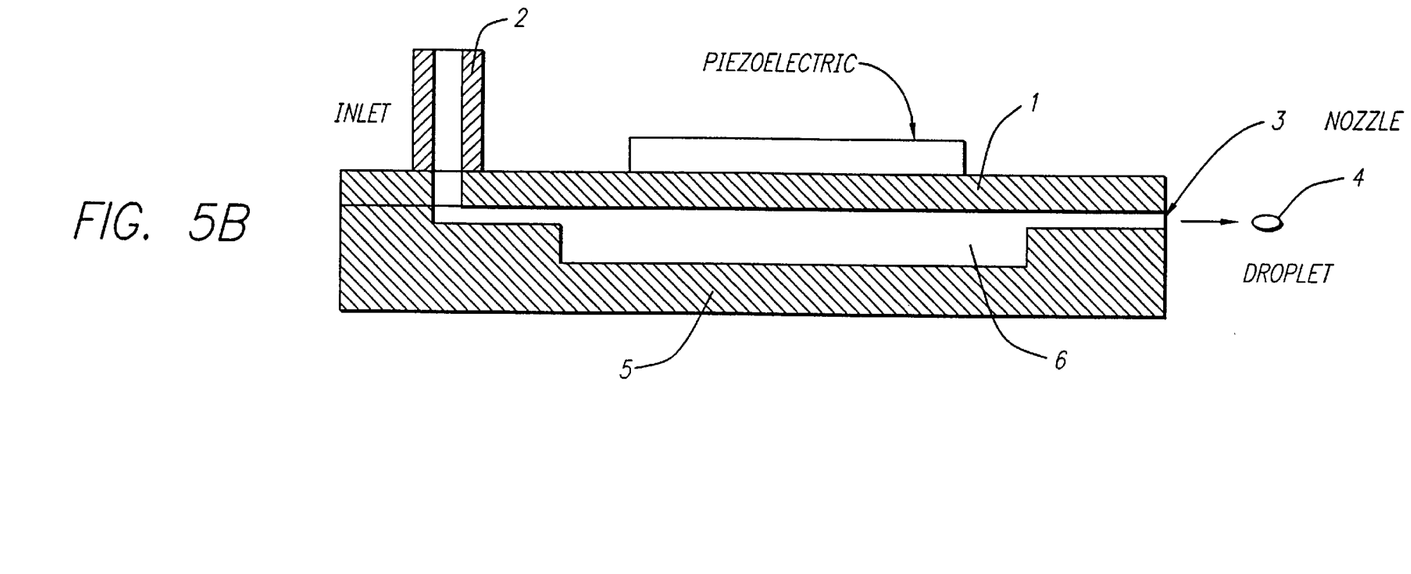

The solution of chemical reactant can be added to the functionalized binding site through utilization of a piezoelectric pump (FIG. 5) in an amount where the solution of chemical reactant at each binding site is separate from the solution of chemical reactant at other binding sites by surface tension. As described more fully infra, in the pump depicted in FIG. 5, reactant solution is inserted through the inlet (2) into the chamber (6) formed between the upper (1) and lower (5) plates of the piezo. Application of a voltage difference across the upper and lower plates causes compression of the piezo, forcing a microdroplet (4) out through the nozzle (3).

Figure 3:
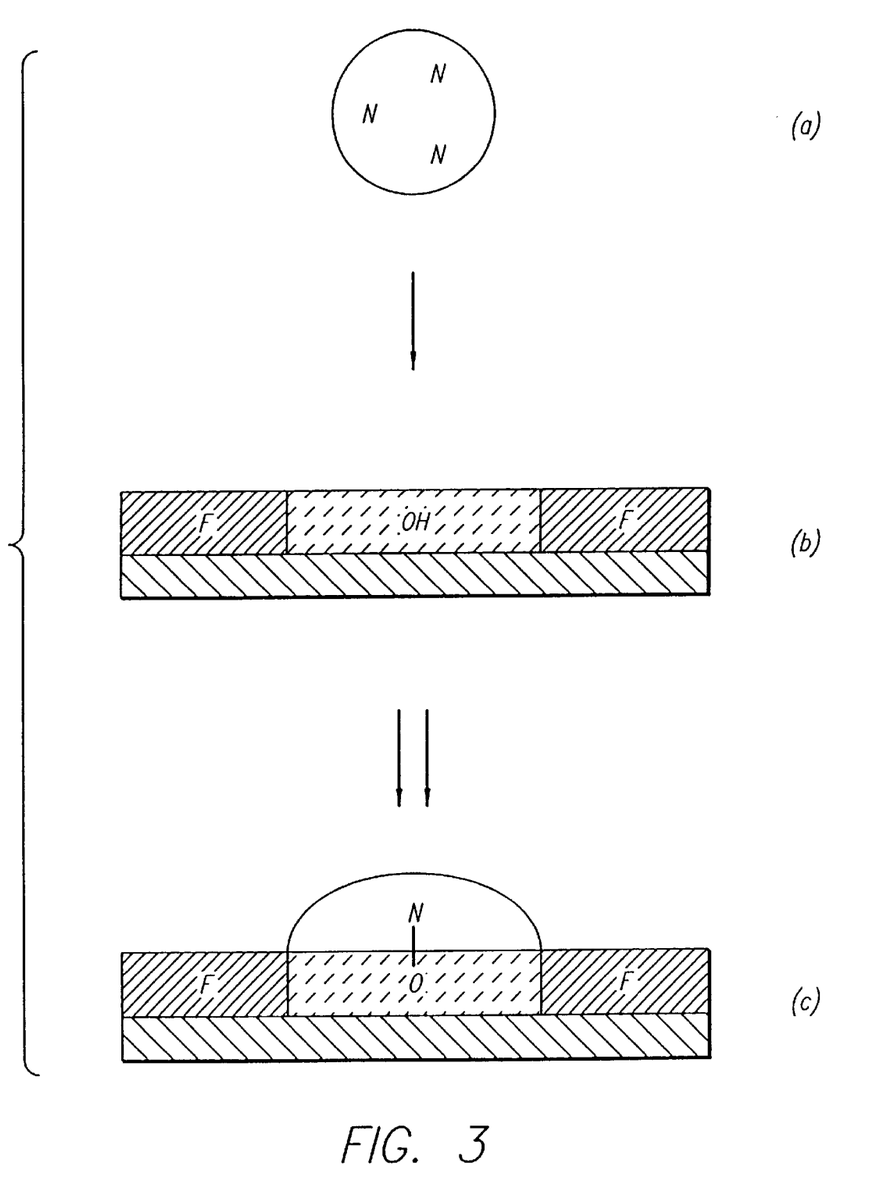
FIG. 3: Surface tension wall effect at the dot-interstice interface. The droplet containing solid phase synthesis reagents does not spread beyond the perimeter of the dot due to the surface tension wall.

FIG. 3 depicts the deposition of the reactant solution on a functionalized binding site and subsequent reaction with the surface. A micro-droplet of solution (FIG. 3(a)) is deposited on the functionalized binding site (center cross-hatched region in FIG. 3(b)). Because of the differences in wetting properties of the reactant solution on the functionalized binding site and the surrounding surface, the micro-droplet of the reactant solution beads on the functionalized binding site and the reactants in solution react with the surface (FIG. 3(c)).

The piezoelectric pump that may be utilized in the invention delivers minute droplets of liquid to a surface in a very precise manner. The pump design is similar to the pumps used in ink jet printing. The picopump is capable of producing 50 micron or 65 picoliter droplets at up to 3000 Hz and can accurately hit a 250 micron target in a 900° C. oven at a distance of 2 cm in a draft free environment. Preferred embodiments of the apparatus according to the invention are set forth in Example 3.

Alternative pump designs should take into account the following physical and mechanical considerations for reliable performance to be obtained. When a non-compressible fluid inside of a pumping cavity is subjected to a rapid strong pressure pulse, the direction of flow of the liquid from the cavity is determined primarily by the inertial resistance of the liquid displaced. There is more liquid, and thus resistance to flow, on the inlet side than through the nozzle port. The column of liquid that is forced out of the nozzle begins to neck off as a result of surface tension: The stream breaks as the piezoelectric is de-energized, with the remaining column of liquid drawn back into the nozzle. The droplet that has necked off continues its flight with the velocity it achieved in the initial acceleration. Typically, the ejection velocity is about 1–2 meters/sec.

In normal printing applications using 150 micron drops of viscous water-based inks, the head speed is typically about 0.5 meter/sec. This motion adds a transverse velocity component to the droplet trajectory and can affect aiming accuracy. It may also cause the drop to skip when it hits a surface. Droplets fired from a stationary head tend to evaporate more slowly because they follow in the vapor trail of the preceding drop. The heads work most reliably when the inlet supply lines are not required to flex and the liquids are not subjected to acceleration forces.

The size of the drop is determined primarily by the surface tension of the solution and by the diameter of the pump nozzle. The smaller the droplet, the faster it will evaporate and the more its trajectory will be affected by drafts. Nozzles smaller than 25 microns tend to become plugged with dust particles. For water, the drop diameter is approximately 1.5 times the nozzle diameter. Typically, drops will not vary in size by more than 5%. We have shown that the jet will also successfully eject a variety of polar solvents, including $CH_3CN$ and MeOH. With these less viscous solvents, too forceful an ejection pulse may result in the formation of a series of trailing satellite droplets in addition to the primary drop. The duration of the pulse also affect satelliting.

After the cavity has returned to its original state, a period of time must be allowed for the nozzle to refill by capillary action before another cycle of pulsing can be initiated. It is important for the nozzle refill only to the top of the orifice, but the liquid meniscus not spread out onto the front face of the jet. This is prevented by silanizing the face to reduce its surface tension. The head is also operated under slight negative pressure to prevent overfilling. The aim of the drop is in the axial direction of the nozzle, but defects in the face coating can affect the trajectory.

Arrays of nozzles with up to 64 independent pumping chambers but a common inlet supply have been fabricated. It is important that each chamber inlet have some restriction so that operation of one pumping chamber does not affect the others. The separation between nozzles is typically 400 microns for printing applications, but denser arrays can be produced either by interleaving the transverse motion of the target or decreasing the nozzle spacing.

EXAMPLE 1

Preparation of Array Plates Ready for Oligonucleotide or Peptide Assembly

The hybridization array is synthesized on a glass plate. The plate is first coated with the stable fluorosiloxane 3-(1,1-dihydroperfluoroctyloxy) propyltrieth-oxysilane. A $CO_2$ laser is used to ablate off regions of the fluorosiloxane and expose the underlying silicon dioxide glass. The plate is then coated with glycidyloxypropyl trimethoxysilane, which reacts only on the exposed regions of the glass to form a glycidyl epoxide. The plate is next treated with hexaethyleneglycol and sulfuric acid to convert the glycidyl epoxide into a hydroxyalkyl group, which acts as a linker arm. The hydroxyalkyl group resembles the 5'-hydroxide of nucleotides and provides a stable anchor on which to initiate solid phase synthesis. The hydroxyalkyl linker arm provides an average distance of 3–4 nm between the oligonucleotide and the glass surface. The siloxane linkage to the glass is completely stable to all acidic and basic deblocking conditions typically used in oligonucleotide or peptide synthesis. This scheme for preparing array plates is illustrated in FIGS. 2(A) and 2(B) and was previously discussed.

EXAMPLE 2

Assembly of Oligonucleotides on the Array Plates

The hydroxyalkylsiloxane surface in the dots has a surface tension of approximately $\gamma=47$, whereas the fluoroxysilane has a surface tension of $\gamma=18$. For oligonucleotide assembly, the solvents of choice are acetonitrile, which has a surface tension of $\gamma=29$, and diethylglycol dimethyl ether. The hydroxyalkylsiloxane surface is thus completely wet by acetonitrile, while the fluorosiloxane masked surface between the dots is very poorly wet by acetonitrile. Droplets of oligonucleotide synthesis reagents in acetonitrile are applied to the dot surfaces and tend to bead up, as shown in FIG. 3. Mixing between adjacent dots is prevented by the very hydrophobic barrier of the mask. The contact angle for acetonitrile at the mask-dot interface is approximately $\theta=43°$. The plate effectively acts as an array microliter dish, wherein the individual wells are defined by surface tension rather than gravity. The volume of a 40 micron droplet is 33 picoliter. The maximum volume retained by a 50 micron dot is approximately 100 picoliter, or about 3 droplets. A 100 micron dot retains approximately 400 picoliter, or about 12 droplets. At maximum loading, 50 micron and 100 micron dots bind about 0.07 and 0.27 femtomoles oligonucleotide, respectively.

Figure 4:
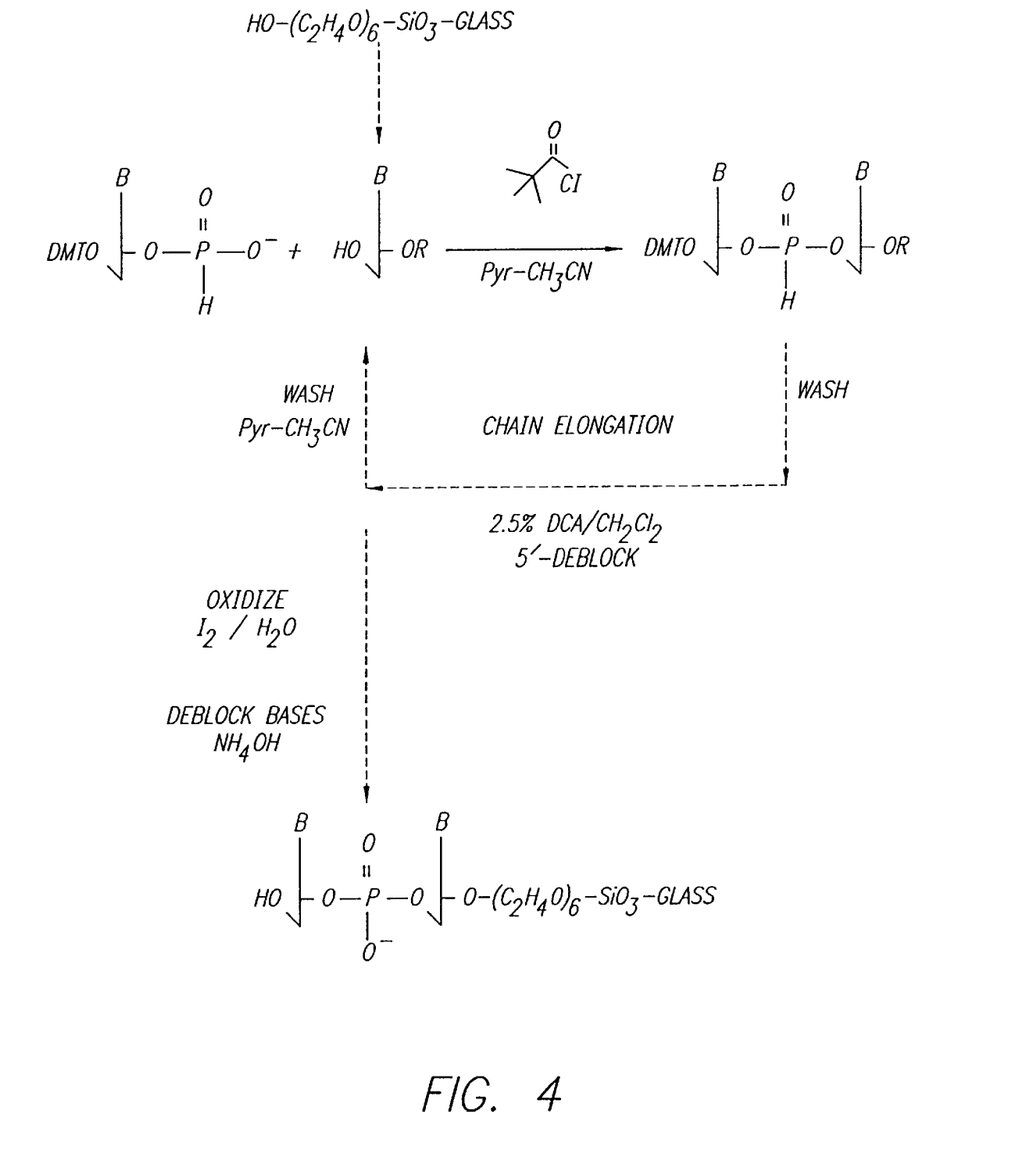
FIG. 4: Hydrogen-phosphonate solid phase oligonucleotide synthesis on an array surface prepared according to Example 1.

Assembly of oligonucleotides on the prepared dots (FIG. 2B, bottom) is carried out according to the H-phosphonate procedure (FIG. 4), or by the phosphoroamidite method. Both methods are well known to those of ordinary skill in the art. Oligonucleotide and Analogs, A Practical Approach (F. Eckstein ed., 1991). Delivery of the appropriate blocked nucleotides and activating agents in acetonitrile is directed to individual dots using the picopump apparatus described in Example 3. All other steps, (e.g., DMT deblocking, washing) are performed on the array in a batch process by flooding the surface with the appropriate reagents. An eight nozzle piezoelectric pump head is used to deliver the blocked nucleotides and activating reagents to the individual dots, and delivering droplets at 1000 Hz, requires only 32 seconds to lay down a 512×512 (262 k) array. Since none of the coupling steps have critical time requirements, the difference in reaction time between the first and last droplet applied is insignificant.

EXAMPLE 3

Construction of Piezoelectric Impulse Jet Pump Apparatus

Piezoelectric impulse jets are fabricated from Photoceram (Corning Glass, Corning, N.Y.), a UV sensitive ceramic, using standard photolithographic techniques to produce the pump details. The ceramic is fired to convert it to a glassy state. The resulting blank is then etched by hydrogen fluoride, which acts faster in exposed then in nonexposed areas. After the cavity and nozzle details are lapped to the appropriate thickness in one plate, the completed chamber is formed by diffusion bonding a second (top) plate to the first plate. The nozzle face is lapped flat and surface treated, then the piezoelectric element is epoxied to the outside of the pumping chamber. When the piezoelectric element is energized it deforms the cavity much like a one-sided bellows, as shown in FIG. 5.

To determine the appropriate orifice size for accurate firing of acetonitrile droplets, a jet head with a series of decreasing orifice sizes is prepared and tested. A 40 micron nozzle produces droplets of about 65 picoliter.

A separate nozzle array head is provided for each of the four nucleotides and a fifth head is provided to deliver the activating reagent for coupling. The five heads are stacked together with a mechanically defined spacing. Each head has an array of eight nozzles with a separation of 400 microns.

Figure 6:
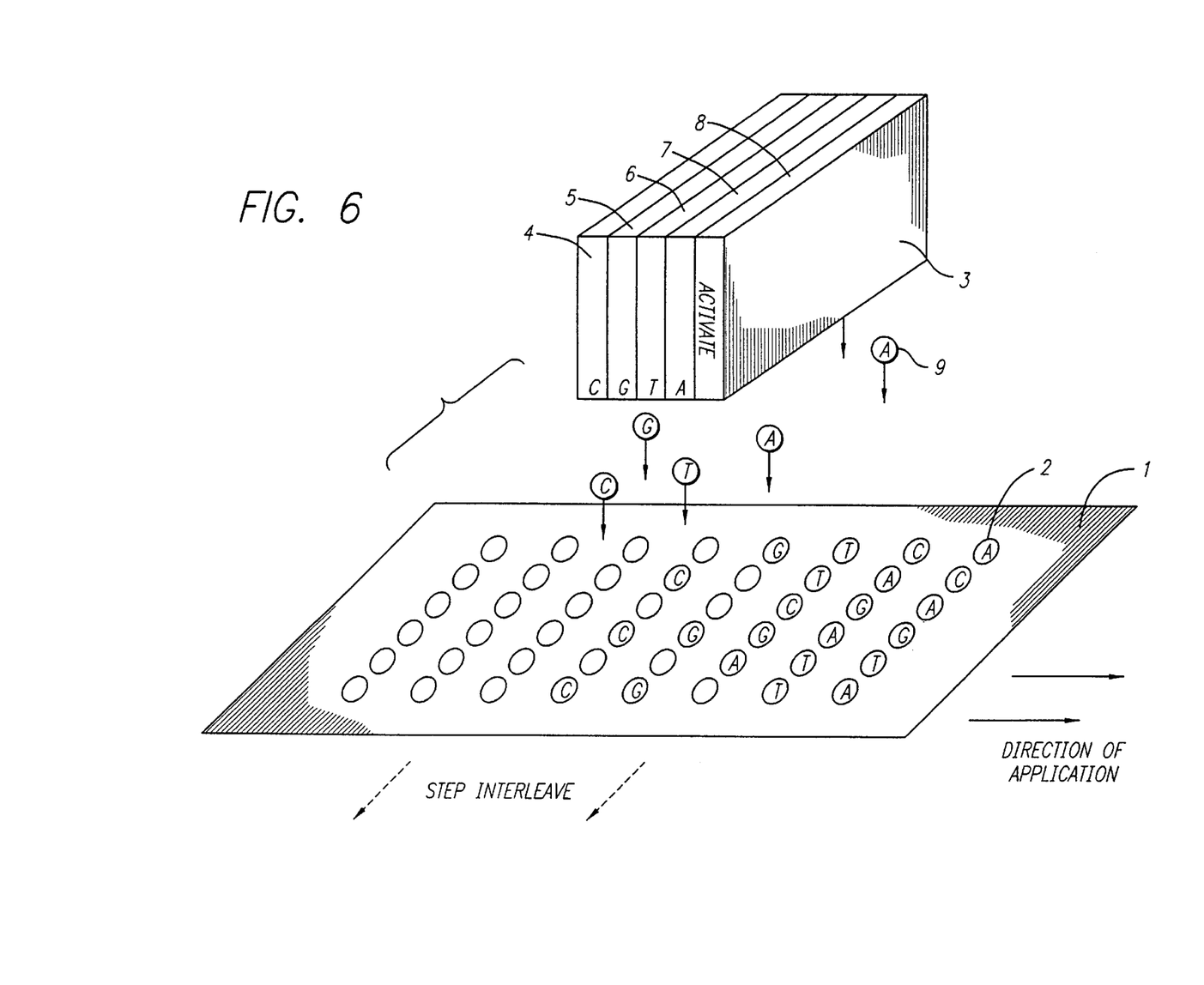
FIG. 6: Use of a piezoelectric impulse jet head to deliver blocked nucleotides and activating agents to individual dots on an array plate. The configuration shown has a stationary head/moving plate assembly.

The completed pump unit is assembled with the heads held stationary and the droplets fired downward at a moving array plate as shown in FIG. 6. The completed pump unit assembly (3) consists of nozzle array heads (4–7) for each of the four nucleotidase and a fifth head (8) for activating reagent. When energized, a microdroplet (9) is ejected from the pump nozzle and deposited on the array plate (1) at a functionalized binding site (2).

Figure 7:
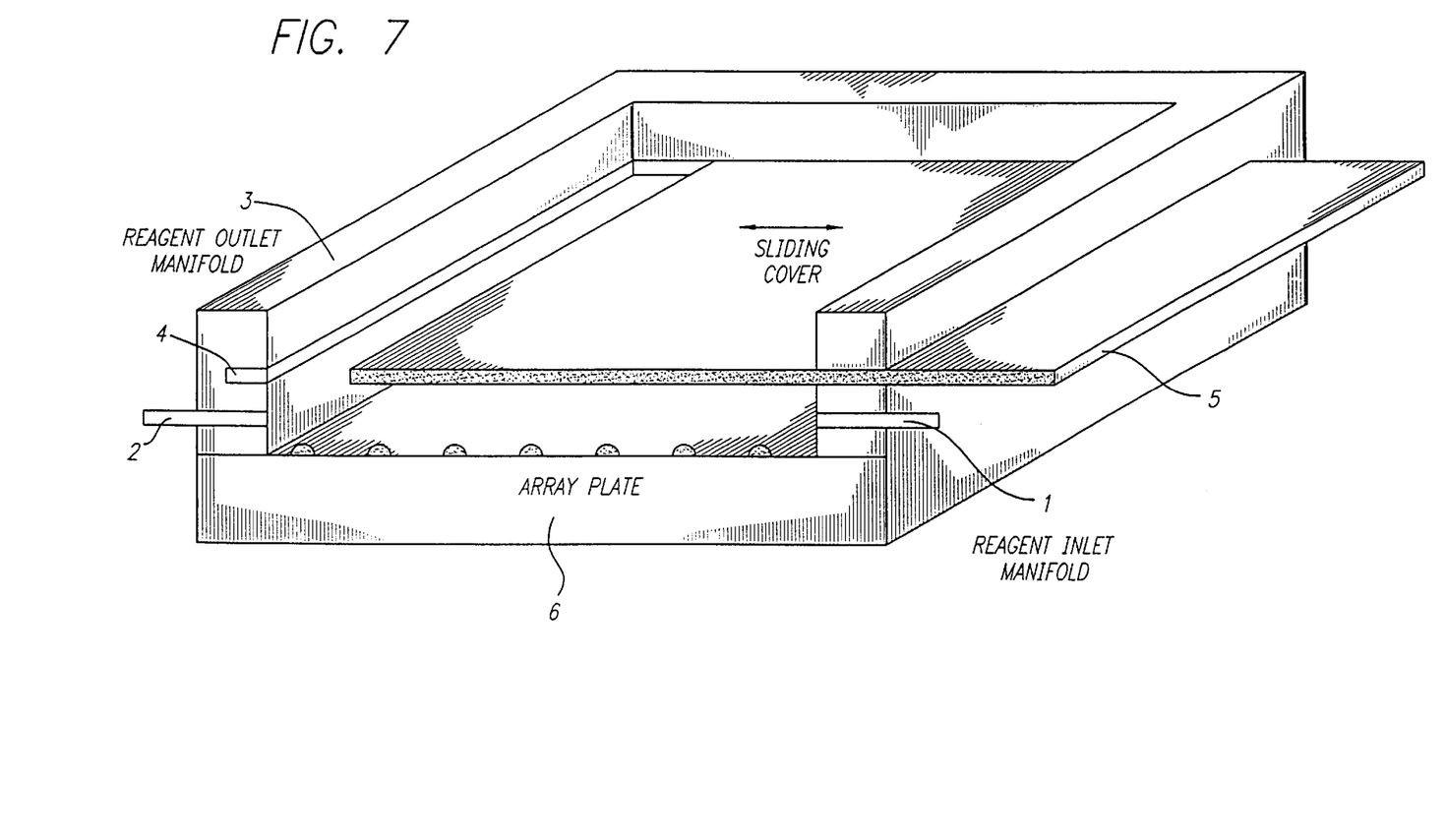
FIG. 7: Enclosure for array reactions showing array plate, sliding cover and manifolds for reagent inlet and outlet.

A plate holding the target array is held in a mechanical stage and is indexed in the X and Y planes beneath the heads by a synchronous screw drives. The mechanical stage is similar to those used in small milling machines, microscopes and microtomes, and provides reproducible positioning accuracy better than 2.5 microns or 0.1 mil. As shown in FIG. 7, the plate holder (3) is fitted with a slotted spacer (4) which permits a cover plate (5) to be slid over the array (6) to form an enclosed chamber. Peripheral inlet (1) and outlet (2) ports are provided to allow the plate to be flooded for washing, application of reagents for a common array reaction, or blowing the plate dry for the next dot array application cycle.

Both the stage and head assembly are enclosed in a glove box which can be evacuated or purged with argon to maintain anhydrous conditions. With the plate holder slid out of the way, the inlet lines to the heads can be pressurized for positive displacement priming of the head chambers or flushing with clean solvent. During operation, the reagent vials are maintained at the ambient pressure of the box.

With a six minute chemistry cycle time, the apparatus can produce 10-mer array plates at the rate of 1 plate or $10^6$ oligonucleotides per hour.

EXAMPLE 4

Use of Oligonucleotide Array Plates to Determine the Nucleotide Sequence of a Target Nucleic Acid The oligonucleotide array plate is prepared as described in Examples 1 and 2, using the apparatus described in Example 3. The array contains oligonucleotides having 10 nucleotides each (10-mers). The synthesis is carried out such that each oligonucleotide element, moving in a 5'-3' direction, is identical to the preceding element in nucleotide sequence, except that it deletes the 5'-most nucleotide, and adds a new 3'-most oligonucleotide. In this way the total array represents every possible permutation of the 10-mer oligonucleotide. Oligonucleotides are spaced at 7 nm intervals to provide an oligonucleotide loading density of $3.4 \times 10^{-12}$ moles/cm$^2$, or $2.6 \times 10^{-16}$ moles per 100 micron element. The target nucleic acid is used to probe the oligonucleotide array plate. The probe is labelled with 1000 Ci/nmol P$^{32}$. The labelled probe is contacted with the oligonucleotide array plate for hybridization in a 10 nM solution of probe in 3M Me$_4$NCl at 42° C. At 10% hybridization and wash efficiency, each oligonucleotide element dot having an exact match with the probe binds 26 attomoles of probe. Radiolabel binding is detected using a Bio-Image Analyzer™ (Fuji, Waltham, Mass.). The pattern of binding is assessed and the nucleotide sequence of the probe nucleic acid is determined by ordering the nucleotide sequence according to the known sequences of the oligonucleotide elements, as shown in FIG. 1.

Figure 1:
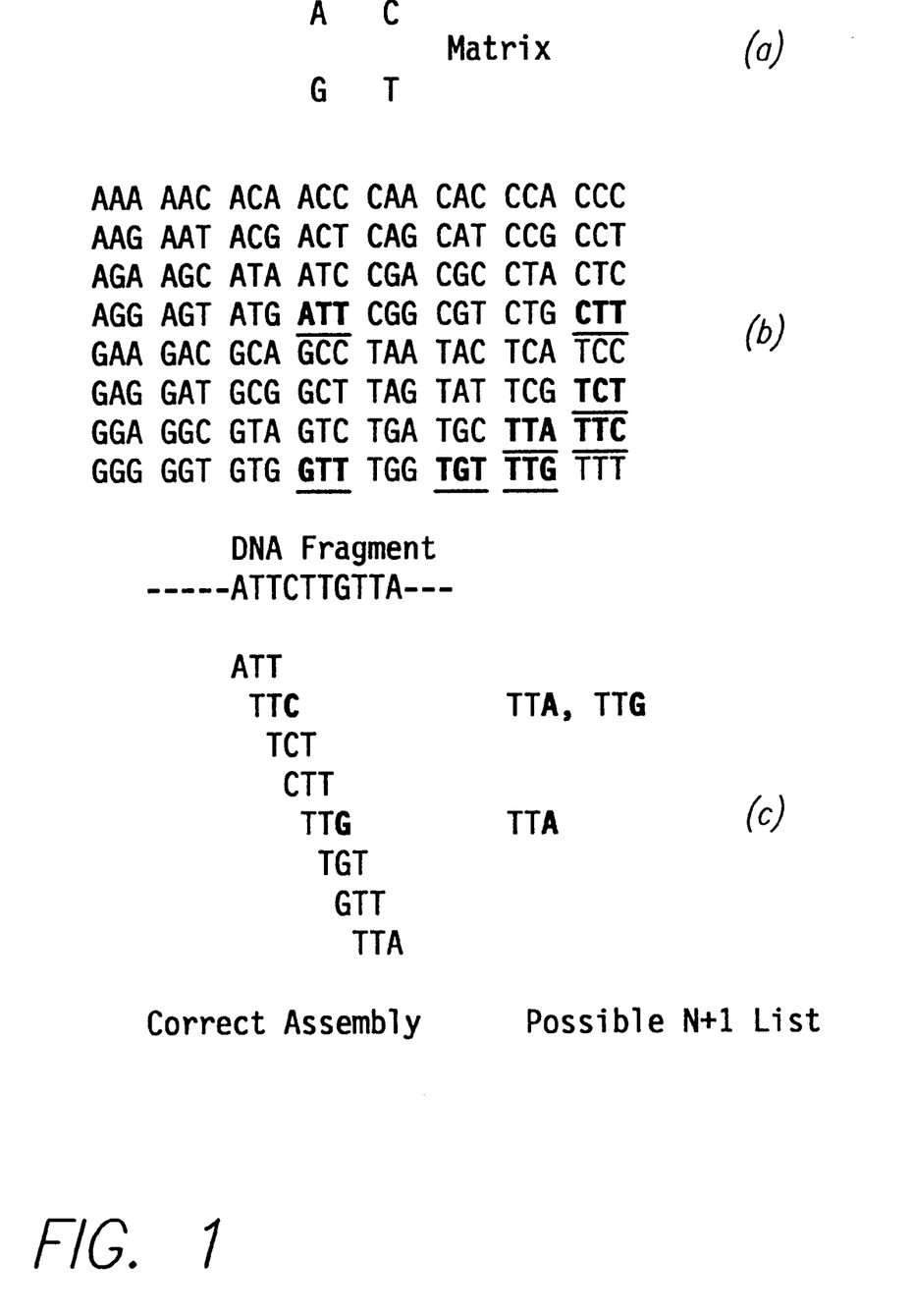
FIG. 1: Hybridization analysis using arrays of trimers. Individual dots that have bound the DNA fragment are underlined.

FIG. 1 depicts a sequencing arrangement based on a matrix of trimer oligonucleotides bound to the array plate. FIG. 1(a) is the basic matrix consisting of the four nucleotides. FIG. 1(b) is the complete trimer matrix, representing each of the 4$^3$ trimer permutations. The underlined elements in the array represent sites to which the target nucleic acid is bound. FIG. 1(c) depicts how a sequence complementary to the target nucleic acid is constructed from the known sequences of the sites to which the target nucleic acid is bound.

What is claimed is:

1. A method for conducting chemical reactions between a solution of a chemical reactant and an array of functionalized binding sites on a support surface comprising adding the solution of chemical reactant to the functionalized binding site in an amount where the solution of chemical reactant at each binding site is separate from the solution of chemical reactant at other binding sites by surface tension.

2. A method of making nucleic acid array plates comprising:
    a) coating a support surface with a positive or negative photoresist substance which is subsequently exposed to light and developed to create a pattern of a first exposed region and a photoresist coated region on the support;
    b) reacting said first exposed region with a reagent to form a stable hydrophobic matrix on said first exposed region;
    c) removing the remaining photoresist coat on said photoresisted coated region so as to form a second exposed region; and
    d) adding at least a first nucleic acid coupling reagent to at least one area of said second exposed region on the nucleic acid array plate.

3. A method of making nucleic acid array plates comprising:
    a) coating a support surface with a positive or negative photoresist substance which is subsequently exposed to light and developed to create a pattern of a first exposed surface and a photoresist coated surface on the support;
    b) reacting said first exposed surface with a reagent to form a stable hydrophobic matrix on said first exposed surface;
    c) removing the photoresist coat on said photoresisted coated surface so as to form a second exposed surface;
    d) reacting said second exposed surface with a second reagent so as to convert said second exposed surface to functionalized hydrophilic binding sites; and
    e) adding at least a first nucleic acid coupling reagent to at least one of said functionalized hydrophilic binding sites.

4. A method of making nucleic acid array plates comprising the step of forming a pattern of functionalized hydrophilic binding sites on a support surface, wherein said functionalized hydrophilic binding sites are chemically reactive to bind nucleic acids in an aqueous solution deposited thereon, and wherein said functionalized hydrophilic binding sites are more polar than their surrounding surface to cause separation of said aqueous solution at one binding site from aqueous solutions at adjacent binding sites.

5. The method according to claim 2, 3, or 4, wherein said support surface comprising a covalently linked layer of inert siloxane.

6. The method according to claim 5, wherein said inert siloxane is tridecafluro-1,1,2,2-tetrahydrooctyl siloxane.

7. The method according to claim 3 or 4, wherein said functional hydrophilic binding sites comprise siloxane compounds selected from the group consisting of hydroxyalkyl siloxane, dihydroxyalkyl siloxanes, and aminoalkyl siloxanes.

8. The method of making array plates according to claim 2 or 3, wherein said first nucleic acid reagent comprises a first nucleotide.

9. The method of making array plates according to claim 8, further comprising adding additional nucleotides to said first nucleotide.

10. The method according to claim 1, 2, 3, or 4, wherein said support surface has 10–10$^4$ functionalized binding sites per cm$^2$.

11. The method according to claim 10, wherein each functionalized binding site is about 50–2000 microns diameter.

12. The method according to claim 1, 2, 3, or 4, wherein said support surface is glass.

13. The method according to claim 1, 2, 3, or 4, wherein said support surface is a derivatized polymer selected from the group consisting of nylon, polyethylene, polypropylene, polystyrene and polytetrafluorethylene.

14. The method of claim 1 wherein the area of the support surface of the functionalized binding site has a higher surface tension relative to the support surface surrounding each functionalized binding site.

15. The method of claim 1 wherein the volume of the chemical reactant solution is 50 picoliter to 2 microliter.

16. The method of claim 1 wherein the chemical reaction between the chemical reactant and functionalized binding site forms covalent bonds.

17. The method of claim 1 wherein chemical reactant reacts with the functionalized binding site by non-covalent binding interactions.

18. The method of claim 2 or 3 where said nucleic acid coupling reagent is a phosphoramidite.

19. The method of claim 2 or 3 where said nucleic acid coupling reagent is an H-phosphonate.

* * * * *